(12) United States Patent
Lee et al.

(10) Patent No.: US 6,635,785 B1
(45) Date of Patent: Oct. 21, 2003

(54) METHOD FOR SYNTHESIZING HYDRAZODICARBONAMIDE

(75) Inventors: Chun-Hyuk Lee, Seoul (KR); Sang-Jin Han, Kyungki-do (KR)

(73) Assignee: J&J Chemical Co., Ltd., Incheon (KR)

( * ) Notice: Subject to any disclaimer, the term of this patent is extended or adjusted under 35 U.S.C. 154(b) by 0 days.

(21) Appl. No.: 10/169,127

(22) PCT Filed: Mar. 7, 2000

(86) PCT No.: PCT/KR00/00180

§ 371 (c)(1),
(2), (4) Date: Jun. 27, 2002

(87) PCT Pub. No.: WO01/49652

PCT Pub. Date: Jul. 12, 2001

(30) Foreign Application Priority Data

Jan. 7, 2000 (KR) .................................... 2000-0000691

(51) Int. Cl.$^7$ .............................................. C07C 28/00
(52) U.S. Cl. ......................................................... 564/35
(58) Field of Search ...................................... 564/35, 34

(56) References Cited

U.S. PATENT DOCUMENTS

| | | | | |
|---|---|---|---|---|
| 3,227,753 | A | * | 1/1966 | Mehr et al. .................... 564/35 |
| 3,969,466 | A | * | 7/1976 | Brown et al. .................. 564/35 |
| 4,049,712 | A | * | 9/1977 | Schirmann et al. ........... 564/35 |
| 4,176,135 | A | * | 11/1979 | Ohno et al. ................... 564/35 |
| 6,472,560 | B2 | * | 10/2002 | Jautelat et al. ................ 564/35 |

OTHER PUBLICATIONS

CA:85:77700 abs of DE 2452016 May 1976.*
CA:91:192851 abs of PL 102400 Mar. 1979.*
CA:136:233883 abs of JP 2002069049 Mar. 2002.*

* cited by examiner

Primary Examiner—Jean F. Vollano
(74) Attorney, Agent, or Firm—Staas & Halsey LLP

(57) ABSTRACT

A method for synthesizing hydrazodicarbonamide (HDCA) by a reaction of monohalobiuret metal salt having the formula 1 or 2, which is derived from biuret, and ammonia, wherein M is a metal and X is a halogen. The monohalobiuret metal salt is inexpensive and easy to synthesize and thus a great yield of HDCA can be obtained from the monohalobiuret metal salt at low cost.

15 Claims, No Drawings

METHOD FOR SYNTHESIZING HYDRAZODICARBONAMIDE

This application is a 371 of PCT/KR00/00180 filed Mar. 7, 2000, now WO 01/49652.

1. Technical Field

The present invention relates to a method of synthesizing hydrazodicarbonamide, and more particularly, to a method for synthesizing hydrazodicarbonamide in high yield at low cost.

2. Background Art

Hydrazodicarbonamide has been used as a source material for azodicarbonamide which is a widely used azo series foaming agent. The following reaction 1 shows that azodicarbonamide (2) can be synthesized by oxidizing hydrazodicarbonamide (1) with an appropriate oxidizing agent.

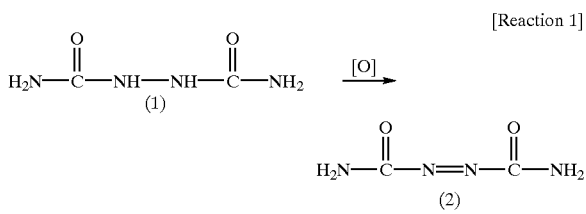

[Reaction 1]

Hydrazodicarbonamide (1) is derived from a reaction of hydrazine (3) and urea (4), which is shown in the following reaction 2.

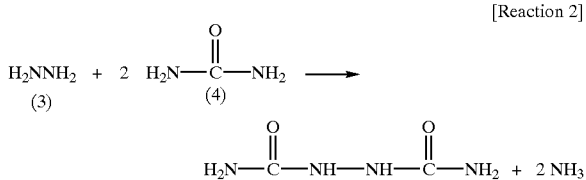

[Reaction 2]

The synthesis of hydrazine, which is one of the reactants, is very expensive and complicate, while urea can be relatively easily obtained at low cost.

Typically, hydrazine is synthesized by the Raschig Process or a method using ketazine. However, hydrazine synthesized by these methods should be subjected to additional condensation or hydrolysis, and wastes huge energy and requires complicate equipment, thus increasing the manufacturing cost.

Another synthesis method of hydrazine is the urea process. According to the urea process, hydrazine is obtained by a reaction between urea and sodium hypochlorite, which is expressed as the following reaction 3.

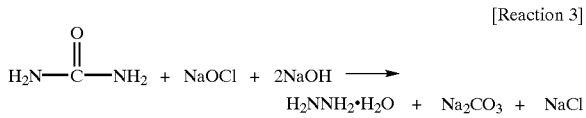

[Reaction 3]

However, such a urea process consumes excess sodium hydroxide and produces sodium carbonate as a byproduct, which must be eliminated. Due to the cost and energy required for the elimination of sodium carbonate, the production cost of hydrazine is inevitably increased, adversely affecting in an environmental aspect.

Synthesis of hydrazodicarbonamide by the urea process is expressed as the following reaction 4.

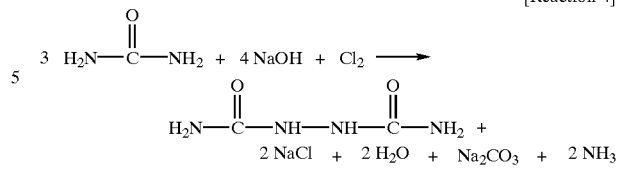

[Reaction 4]

Reaction 4 shows that excess reactants, including 3 moles of urea, 4 moles of sodium hydroxide and 1 mole of chlorine ($Cl_2$), are consumed for producing 1 mole of hydrazodicarbonamide.

As previously described, using hydrazine for the synthesis of hydrazodicarbonamide is an expensive and complicated process, and is undesirable in an environmental aspect.

Another approach for the synthesis of hydrazodicarbonamide is to use semicarbazide instead of the expensive hydrazine. The following reaction 5 illustrates the synthesis of semicarbazide. Urea and sodium hypochlorite are reacted to obtain monochlbrourea sodium salt as an intermediate and then reacted with excess ammonia in the presence of a catalyst to give semicarbazide.

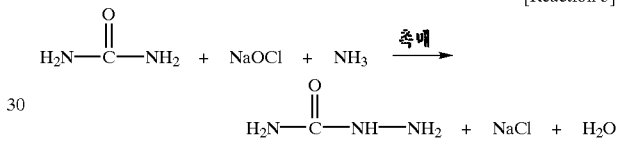

[Reaction 5]

However, the problem with this reaction is the need for excess ammonia. The amount of ammonia required is about 500 times the intermediate, monochlorourea sodium salt. Alternatively, an expensive catalyst should be used instead of reducing the amount of ammonia added for the reaction, thus raising the cost.

In addition, on more additional reaction for conversion of the obtained semicarbazide to hydrazodicarbonamide is required, which is expressed as the following reaction 6.

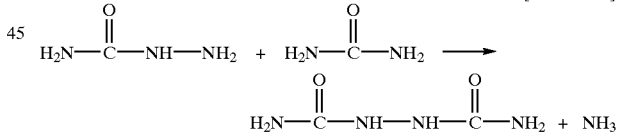

[Reaction 6]

DISCLOSURE OF THE INVENTION

An object of the present invention is to provide a method of synthesizing a great yield of hydrazodicarbonamide in a simple and inexpensive manner.

The above object of the present invention is achieved by a method for synthesizing hydrazodicarbonamide by a reaction of monohalobiuret metal salt having the formula 1 or 2, and ammonia in a solvent

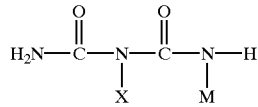

[Formula 1]

-continued

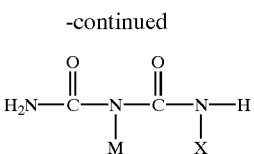

[Formula 2]

where M is a metal and X is a halogen.

The above object and advantages of the present invention will become more apparent by describing in detail preferred embodiments thereof.

BEST MODE FOR CARRYING OUT THE INVENTION

An example of the synthesis of hydrazodicarbonamide (HDCA) according to the present invention is expressed as the following reaction 7.

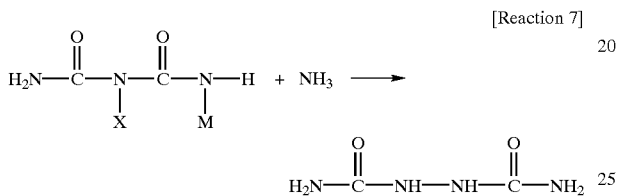

[Reaction 7]

where M is a metal and X is a halogen.

In Reaction 7, monohalobiuret metal salt as a reactant may be derived by reacting the biuret having the formula 3 below with a metal hypohalogen compound, or by reacting the biuret with a halogen element and a base.

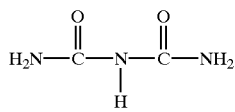

[Formula 3]

The synthesis reaction for HDCA according to the present invention may be carried out at a temperature of 30 to 150° C.

For Reaction 7 ammonia may be liquid ammonia, gaseous ammonia or ammonia water, but liquid ammonia is preferred. If ammonia water is selected as a source of ammonia, the concentration of ammonia water may be in the range of 10 to 50%.

The amount of ammonia used may be 1 to 1000 moles, but preferably 2 to 500 moles, with respect to 1 mole of monohalobiuret metal salt.

The solvent for Reaction 7 may be water or a solvent mixture containing water and an organic solvent, but water is preferred. If the solvent mixture is selected, the organic solvent may be at least one selected from the group consisting an aprotic polar solvent and a protic polar solvent having a dielectric constant of 50 or less. For example, the organic solvent includes methanol, ethanol, propanol, isopropanol, dimethylformamide, tetrahydrofuran and acetonitrile.

Preferably, the amount of organic solvent is 0.1 to 50 times by weight, but preferably 0.2 to 3.0 times by weight based on the amount of water.

A catalyst may be further added for reduction of reaction time and reaction efficiency. The catalyst may be sulfates, chlorides, carbonates and hydroxides of transition metal or alkali metal, and heavy metal salts of carboxylic acids. The amount of catalyst added may be 0.001 to 1 moles, but preferably 0.01 to 0.5 moles, with respect to 1 mole of monohalobiuret metal salt.

Alternatively, an inorganic acid such as hydrochloric acid, sulfuric acid and nitric acid may be used as a catalyst. Preferably, the amount of inorganic catalyst is 0.5 to 3.0 moles with respect to 1 mole of monohalobiuret metal salt.

In the reactions of the present invention, preferably the metal designated M is sodium, potassium or calcium, and the halogen element designated X is fluorine, chlorine, bromine or iodine.

Hereinafter, the synthesis of HDCA according to the present invention will now be described.

Monohalobiuret metal salt having the formula 1 or 2 hereinabove, as a reactant for the synthesis of HDCA, are prepared by a variety of methods.

One of these methods is to directly react biuret with a metal hypohalogen, compound, which is expressed as the following reaction 8

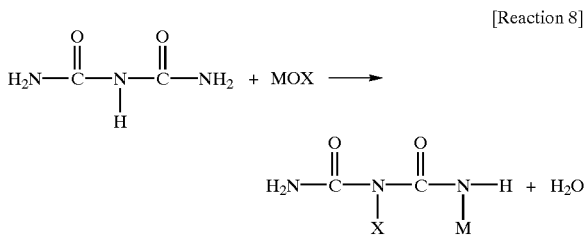

[Reaction 8]

where M is a metal and X is a halogen.

For example, chlorobiuret sodium salt is directly derived from biuret and sodium hypochlorite as expressed in the following reaction 9

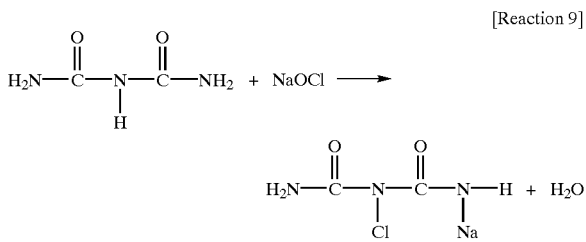

[Reaction 9]

Since Reaction 9 is a kind of exothermic reaction, it is preferable to keep the temperature of the reaction system at low temperatures. Due to thermal stability of chlorobiuret sodium salt produced, the above reaction may be carried out at room temperature, but preferably, within the range of −5 to 35° C.

As for the amount of reactants, preferably, 0.1 to 2 moles of sodium hypochlorite is added with respect to 1 mole of biuret in terms of the reaction efficiency and ease of handling. The produced chlorobiuret sodium salt may be readily used or may be reserved for use in a subsequent reaction.

As another method of preparing monohalobiuret metal salt, biuret is reacted with a halogen element ($X_2$) such as chlorine ($Cl_2$) or a halogen compound to obtain monohalobiuret (5), and a base, but preferably a metal hydroxide such as sodium hydroxide, potassium hydroxide or calcium hydroxide is then added to give monohalobiuret metal salt as a reactant for the synthesis of HDCA according to the present invention, which is expressed as the following reaction 10

[Reaction 10]

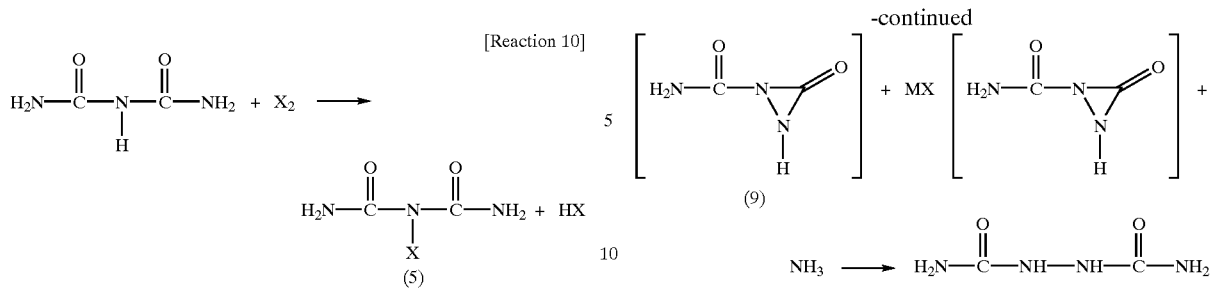

where M is a metal and X is a halogen.

Since the halogenation of biuret for monohalobiuret 5 is also a kind of exothermic reaction, it is preferable to keep the reaction temperature at low temperatures, but more preferably, within the range of −5 to 30° C. in terms of the stability of the reaction.

As a modification of Reaction 10, biuret is mixed with a metal hydroxide and then reacted with halogen to give monohalobiuret metal salt. Since this reaction is also an exothermic reaction, it is preferable to keep the reaction temperature at low temperatures, but more preferably, within the range of −5 to 30° C.

Monohalobiuret metal salt produced is in the form of 3-monohalobiuret metal salt or 1-monohalobiuret metal salt. Here, 3-monohalobiuret metal salt is the major form.

Referring to the following reaction 11, as biuret is reacted with a halogen compound, halogenation occurs at the position of Nitrogen 1 or Nitrogen 3. Due to higher acidity of hydrogen at the position of Nitrogen 3, hydrogen at the position of Nitrogen 3 is substituted by chlorine, resulting in 3-monohalobiuret (6) as the major product. Then, 3-monohalobiuret (6) is subjected to deprotonation to give 3-monohalobiuret metal salt.

Although the possibility of reaction is low, 1-monohalobiuret (7) may be produced by substitution of hydrogen at the position of Nitrogen 1 by chlorine, and deprotonated to produce 1-monohalobiuret metal salt.

[Reaction 11]

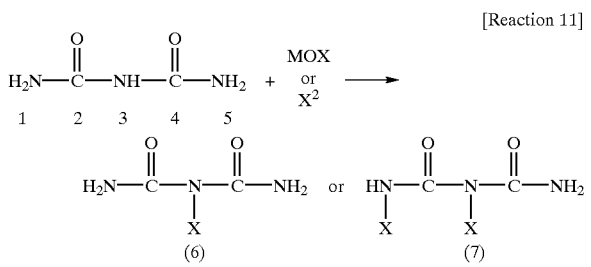

Next, HDCA is synthesized by a reaction of ammonia and monohalobiuret metal salt which is prepared by the previously described method. This synthesis pathway is similar to the Favorskii reaction expressed as the following reaction 12

[Reaction 12]

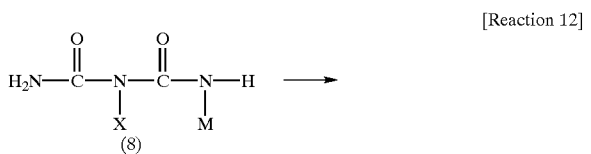

In Reaction 12, the metal halide is cleaved from monohalobiuret metal salt (8) by a reaction of negatively charged nitrogen atoms within its molecule and a N—N bond is formed, resulting in unstable diaziridinone derivative (9). Diaziridinone derivative (9) is immediately reacted with highly reactive ammonia to give HDCA.

In the above-mentioned synthesis reaction for HDCA according to the present invention, a preferred reaction temperature ranges from 30 to 150° C. in terms of higher reaction rate and efficiency.

In addition, ammonia used in the above reaction 12 may be gaseous ammonia, liquid ammonia or ammonia water, but liquid ammonia is preferred in terms of the concentration of reactants and the reaction rate. If ammonia water is selected as a source for ammonia, the concentration of ammonia water may be in the range of 10 to 50%. Preferably, the amount of ammonia added is 1 to 1000 moles, but more preferably, 2 to 500 moles, with respect to 1 mole of monohalobiuret metal salt.

If the synthesis reaction for HDCA is carried out at high temperatures with excess ammonia, the synthesis reaction may be performed under pressure, but more preferably, in the range of 1 to 100 kgf/cm$^2$, which avoids evaporation of ammonia and in turn increases the reaction rate and efficiency.

An advantage of the present invention is a higher yield in the absence of catalyst. However, the reaction time can be reduced with improved reaction efficiency by using a catalyst. The catalyst may be at least one selected from the group consisting of sulfates, chlorides, carbonates and hydroxides of transitioin metal or alkali metal, and heavy metal salts of carboxylic acids. Preferably, the amount of these catalysts is 0.001 to 1 moles, but more preferably 0.01 to 0.5 moles with respect to 1 mole of monohalobiuret metal salt having Formula 1 hereinabove. Alternatively, an inorganic acid such as sulfuric acid, hydrochloric acid or nitric acid may be used as a catalyst in an amount of 0.5 to 3.0 moles with respect to 1 mole of monohalobiuret metal salt.

Meanwhile, a solvent for biuret or the reaction system according to the present invention may be water. In either case, alcohol such as methanol, ethanol, propanol or isopropanol, dimethylformamide, tetrahydrofuran, or acetonitrile may be used as an organic solvent along with water. The amount of organic solvent is not limited, but preferably, the organic solvent is added in an amount of 0.2 to 3.0 times by weight based on water.

The organic solvent may be added at the beginning of the reaction as a solvent for biuret, or after a biuret solution is mixed with a sodium hypochlorite solution.

As previously described, considering that biuret is derived from 2 moles of urea and 1 mole of metal hypohalogen compound is derived from 2 moles of metal hydroxide and 1 mole of halogen compound, 2 moles of urea, 2 moles of metal hydroxide and 1 mole of halogen compound are consumed for obtaining 1 mole of HDCA according to the present invention (refer to Reaction 13 below).

[Reaction 13]

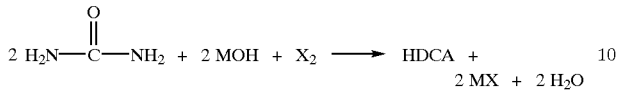

2 MX + 2 H$_2$O where M is a metal and X is a halogen.

The amount of reactants used for HDCA according to the present invention is less than in a conventional technique, thus reducing the manufacturing cost. Also, as opposed to the case of using semicarbazide for the synthesis of HDCA, no additional process is required to give HDCA.

The present invention will now be described in greater detail with reference to the following examples. The following examples are illustrative and not intended to limit the scope of the invention.

EXAMPLES

Preparation of Chlorobiuret Sodium Salt
Preparation 1

229.6 g (0.287 moles) of 12.9% biuret slurry solution was placed in a 2-liter glass reactor and cooled to 5° C. while stirring. To the reactor was added 170 g (0.287 moles) of 12% sodium hypochlorite solution and the temperature of the reaction system was controlled to be 5° C. or less. After completion of adding sodium hypochlorite solution, the reaction product was analyzed by iodine titration method and liquid chromatography. The available chlorine of the reaction solution was 5.0% and the yield was 98%.
Preparation 2

229.6 g (0.287 moles) of 12.9% biuret slurry solution was placed in a 2-liter glass reactor and cooled to 5° C. while stirring. To the reactor was added 223 g (0.575 moles) of 10.3% sodium hydroxide solution. 20.3 g (0.287 moles) of chlorine gas was further added while keeping the temperature of the reaction system at 10° C. or less. After completion of adding chlorine gas, the reaction product was analyzed by iodine titration method and liquid chromatography. The available chlorine of the reaction is solution was 4.2% and the yield was 98%.
Preparation 3

229.6 g (0.287 moles) of 12.9% biuret slurry solution was placed in a 2-liter glass reactor and cooled to 5° C. while stirring. To the reactor was added 20.3 g (0.287 moles) of chlorine gas while keeping the temperature of the reaction solution at 10° C. or less. After the addition of chlorine gas, 223 g (0.575 moles) of 10.3% sodium hydroxide solution was further added and vigorously stirred while keeping the temperature of the reaction system at 5° C. or less. Then, the reaction product was analyzed by iodine titration method and liquid chromatography. The available chlorine of the reaction solution was 4.2% and the yield was 98%.

Synthesis of HDCA

Example 1

399.6 g of the chlorobiuret sodium salt solution prepared in accordance with Preparation 1 was placed in a 2-liter glass reactor and cooled to 10° C. while stirring. To the reactor was added 600 g (8.8 moles) of 25% ammonia water while keeping the temperature of the reaction solution at 10° C. or less. The temperature of the reactor was raised to 100° C. while vigorously stirring and maintained at the same temperature for 30 minutes.

After the reaction was completed, unreacted ammonia was removed and the reaction solution was filtered to give 30.5 g of water-insoluble HDCA in a yield of 90%.

Example 2

The process of Example 1 was followed except that 1.95 g (0.014 moles) of ZnCl$_2$ was further added as a catalyst to the reaction system. 31.5 g of HDCA was obtained in a yield of 93%.

Example 3

The process of Example 1 was followed except that 25.4 ml (0.287 moles) of 35% HCl was further added as a catalyst to the reaction system. 31.2 g of HDCA was obtained in a yield of 92%.

Example 4

The process of Example 1 was followed except that 3.57 g (0.014 moles) of Ni(CH$_3$CO$_2$)$_2$.4H$_2$O was further added as a catalyst to the reaction system. 31.2 g of HDCA was obtained in a yield of 92%.

Example 5

229.6 g (0.287 moles) of 12.9% biuret slurry solution was placed in a 2-liter glass reactor and cooled to 5° C. while stirring. To the reactor was added 170 g (0.287 moles) of 12% sodium hypochlorite solution and the temperature of the reaction system was controlled to be 10° C. or less The temperature of the resultant solution was raised to 100° C. while adding 150 g (8.8 moles) of liquid ammonia to the reaction solution, and maintained at the same temperature for 30 minutes.

After the reaction was completed, unreacted ammonia was removed and the reaction solution was filtered to give 32.2 g of water-insoluble HDCA in a yield of 95%.

Example 6

The process of Example 5 was followed except that 1.95 g (0.014 moles) of ZnCl$_2$ was further added as a catalyst to the reaction system. 32.5 g of HDCA was obtained in a yield of 96%.

Example 7

A biuret slurry solution obtained by suspending 29.6 g (0.287 moles) of biuret in 200 g of ethanol was placed in a 2-liter pressure reactor and cooled to 5° C. while stirring. To the reactor was added 170 g (0.287 moles) of 12% sodium hypochlorite solution and the temperature of the reaction system was controlled to be 10° C. or less. The temperature of the resultant solution was raised to 100° C. while adding 150 g (8.8 moles) of liquid ammonia to the reaction solution, and maintained at the same temperature for 30 minutes.

After the reaction was completed, unreacted ammonia was removed and the reaction solution was filtered to give 28.8 9 of water-insoluble HDCA in a yield of 85%.

Example 8

The process of Example 1 was followed except that the temperature of the reaction solution at the time of adding the sodium hypochlorite solution to the biuret slurry solution was maintained at 20° C., resulting in 31.5 g of HDCA in a yield of 93%.

Example 9

The process of Example 1 was followed except that 25% ammonia water was added in an amount of 200 g (2.93 moles), resulting in 29.5 g of HDCA in a yield of 87%.

Example 10

472.9 g of the chlorobiuret sodium salt solution prepared in accordance with Preparation 2 was placed in a 2-liter glass reactor and cooled to 10° C. while stirring. While adding 150 g (8.8 moles) of liquid ammonia to the reaction solution, the temperature of the resultant solution was raised 100° C. and maintained at the same temperature for 30 minutes.

After the reaction was completed, unreacted ammonia was removed and the reaction solution was filtered to give 32.2 g of water-insoluble HDCA in a yield of 95%.

Example 11

The process of Example 10 was followed except that 472.9 g of the chlorobiuret sodium salt solution prepared in accordance with Preparation 3 was used, resulting in 32.2 g of HDCA in a yield of 95%.

The present invention provides a great yield of HDCA at low cost. HDCA according to the present invention can be directly derived from monohalobiuret metal salt without the need for an additional reaction stage.

What is claimed is:

1. A method for synthesizing hydrazodicarbonamide by a reaction of monohalobiuret metal salt having the formula 1 or 2, and ammonia in a solvent

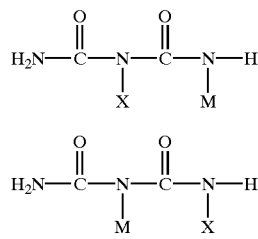

[Formula 1]

[Formula 2]

where M is a metal selected from the group consisting of sodium, potassium and calcium, and X is a halogen selected from the group consisting of fluorine, chloride, bromine and iodine.

2. The method of claim 1, wherein the monohalobiuret metal salt is derived by a reaction between biuret having the following formula 3 and a metal hypohalogen compound

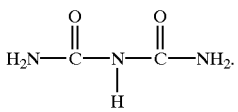

[Formula 3]

3. The method of claim 2, wherein the biuret and the metal hypohalogen compound are reacted in a molar ratio of 0.5:1 to 10:1.

4. The method of claim 1, wherein for preparation of monohalobiuret metal salt, biuret having the following formula 3 is mixed with a metal hydroxide and then reacted with a halogen gas, or the biuret is reacted with a halogen gas and a base is then added to the reaction mixture

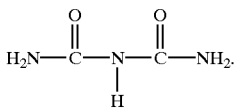

[Formula 3]

5. The method of claim 2, wherein the reaction is carried out at 35° C. or less.

6. The method of claim 3, wherein the reaction is carried out at 35° C. or less.

7. The method of claim 4, wherein the reaction is carried out at 35° C. or less.

8. The method of claim 1, wherein the ammonia is liquid ammonia, gaseous ammonia or ammonia water.

9. The method of claim 1, wherein the monohalobiuret metal salt and ammonia are reacted in a molar ratio of 1:1 to 1:1000.

10. The method of claim 1, wherein the reaction was carried out at a temperature of 30 to 150° C.

11. The method of claim 1, wherein the solvent is water.

12. The method of claim 1, wherein the solvent is a solvent mixture containing water and an organic solvent, and the amount of organic solvent added is 0.1 to 50 times by weight based on the amount of water.

13. The method of claim 12, wherein the organic solvent is at least one selected from the group consisting an aprotic polar solvent and a protic polar solvent having a dielectric constant of 50 or less.

14. The method of claim 1, wherein at least one catalyst selected from the group consisting of sulfates, chlorides, carbonates and hydroxides of transition metal or alkali metal, and heavy metal salts of carboxylic acids, and the amount of catalyst added is 0.001 to 1 moles with respect to 1 mole of monohalobiuret metal salt having the formula 1.

15. The method of claim 1, wherein at least one inorganic catalyst selected from the group consisting of hydrochloric acid, sulfuric acid and nitric acid is further added, and the amount of inorganic catalyst is 0.5 to 3.0 moles with respect to 1 mole of monohalobiuret metal salt having the formula 1.

* * * * *